United States Patent [19]
Richard et al.

[11] Patent Number: 6,045,812
[45] Date of Patent: Apr. 4, 2000

[54] CYCLODEXTRIN DERIVATIVES

[75] Inventors: Herve Richard, Villepinte; Madeleine Leduc, Paris, both of France

[73] Assignee: Societe L'Oreal S.A., Paris, France

[21] Appl. No.: 08/875,729

[22] PCT Filed: Nov. 14, 1996

[86] PCT No.: PCT/FR96/01800

§ 371 Date: Dec. 1, 1997

§ 102(e) Date: Dec. 1, 1997

[87] PCT Pub. No.: WO97/20861

PCT Pub. Date: Jun. 12, 1997

[30] Foreign Application Priority Data

Dec. 4, 1995 [FR] France ................... 95 14318

[51] Int. Cl.⁷ .................. A61K 6/00; A61K 7/00; A61K 31/715; C08B 37/00
[52] U.S. Cl. .................. 424/401; 424/70.1; 514/58; 536/103; 536/124
[58] Field of Search ............... 536/103, 124; 514/58; 424/401, 70.1

[56] References Cited

U.S. PATENT DOCUMENTS 5,447,920  9/1995  Matsuda et al. .................. 514/58

OTHER PUBLICATIONS

*Chem. Pharm. Bull.,* vol. 23, No. 7, issued 1975, Uekam et al., "Inclusion Complexes of Cinnamic Acids with Cyclodextrin Mode of Inclusion in Aqueous Solution," pp. 1421–1430, 1975.

*Primary Examiner*—Gary L. Kunz
*Assistant Examiner*—Everett White
*Attorney, Agent, or Firm*—Burns, Doane, Swecker & Mathis, L.L.P.

[57] ABSTRACT

The invention relates to novel cyclodextrin derivatives of formula (I)

$$CD(OH)_l(OR_1)_m(OR_2)_n \qquad (I)$$

in which:

$OR_1$ represents a screening or antioxidant group or a mixture thereof, $OR_2$ represents an alkyl or hydroxyalkyl radical, l, m and n are statistical values.

The invention also relates to a process for the preparation of these compounds and to the use of these compounds in cosmetics.

13 Claims, No Drawings

CYCLODEXTRIN DERIVATIVES

This application is a 371 of PCT/FR96/01800 filed Nov. 14, 1996.

The present invention relates to novel cyclodextrin derivatives, to a process for their preparation and to their use in cosmetics.

Cyclodextrins are oligosaccharides of formula:

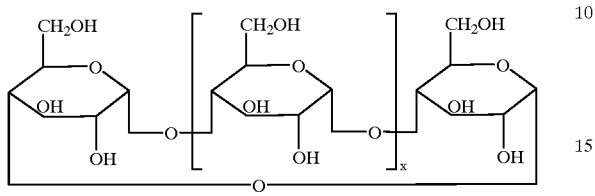

in which x may be a number equal to 4 (which corresponds to α-cyclodextrin), 5 (β-cyclodextrin) or 6 (γ-cyclodextrin).

Cyclodextrins are compounds that are well known, in particular for their ability to form inclusion complexes with active substances.

Moreover, the possibility of substituting one or more hydroxyl groups of cyclodextrins in order to graft active substances has been studied. Thus the article by Berger, Journal of Organic Chemistry, 56, pages 3514–3520, 1991, describes β-cyclodextrins grafted with a single graft of m,m'-disulphonylbenzophenone. The article by Tabushi in Tetrahedron Letters No. 29, pages 2503–2506, 1977, describes β-cyclodextrins grafted with a benzophenone graft via an ester linkage.

However, these grafted compounds bear few active grafts, which limits their activity and their efficacy.

After various studies on cyclodextrins, the Applicant has observed, surprisingly, that it is possible to obtain cyclodextrins having screening and/or antioxidant activity, with a higher level of grafting, thereby making it possible to improve the activity and the efficacy of these compounds.

The subject of the present invention is thus novel cyclodextrin derivatives corresponding to the general formula (I) below:

$$CD(OH)_l(OR_1)_m(OR_2)_n \quad (I)$$

in which

CD represents the basic skeleton of α-, β- or γ-cyclodextrin without the hydroxyl groups, $OR_1$ represents a group, attached to the basic skeleton of the cyclodextrin, in which $R_1$ represents a radical of formula (II), (III), (IV), (V) or (VI) below:

(II)

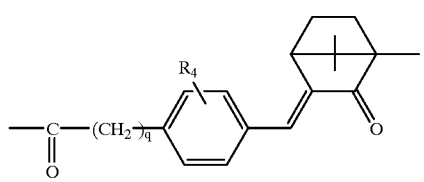

(III)

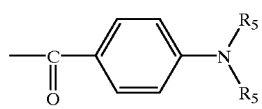

(IV)

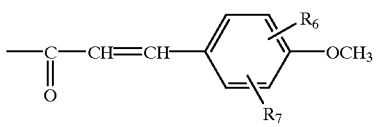

(V)

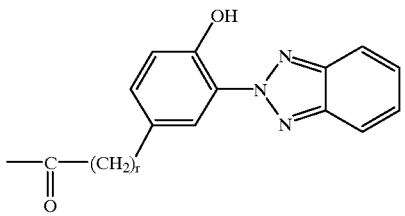

(VI)

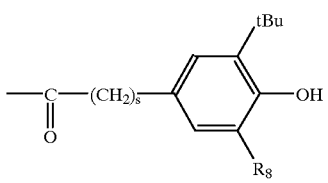

or a mixture thereof, in which formulae $R_4$, $R_6$ and $R_7$ represent a hydrogen atom or a $C_1$–$C_6$alkyl radical or a $C_1$–$C_{12}$alkoxy radical, $R_5$ represents a $C_1$–$C_{12}$alkyl radical, q and r represent an integer equal to 0 or 1, $R_8$ represents H or a $C_1$–$C_8$alkyl radical or a $C_1$–$C_4$alkoxy radical, s is an integer ranging from 0 to 4, $OR_2$ represents a group, attached to the basic skeleton of the cyclodextrin, in which $R_2$ represents a linear or branched $C_1$–$C_4$alkyl radical or a $C_2$–$C_4$hydroxyalkyl radical, it being possible for the hydrogen of the hydroxyl group of the said hydroxyalkyl radical to be substituted with another $C_1$–$C_4$hydroxyalkyl group or with a radical $R_1$ or a mixture thereof, l, m and n are statistical values such that m represents the number of groups $OR_1$ attached directly to the basic skeleton of the cyclodextrin and is a statistical value other than 0, n represents the number of groups $OR_2$ attached directly to the basic skeleton of the cyclodextrin and is a statistical value other than 0, l is a statistical value such that (l+m+n) is equal to 18, 21, 24 depending on whether CD is the basic skeleton of α-, β- or γ-cyclodextrin respectively.

The compounds of formula (I) bearing radicals of formula (II) to (V) are active in screening out solar radiation and those bearing a radical of formula (VI) have antioxidant activity. The compounds of formula (I) bearing both at least one radical of formula (II) to (V) and at least one radical of formula (VI) have screening and antioxidant activity.

$R_2$ preferably denotes a methyl or hydroxypropyl radical, it being possible for the hydrogen of the hydroxyl group of the hydroxypropyl radical to be substituted with another hydroxypropyl group or with a radical $R_1$.

When CD represents the basic skeleton of α-cyclodextrin, n is preferably a value ranging from 3 to 5 and the total number m of groups $R_1$ ranges from 2.5 to 14.

When CD represents the basic skeleton of β-cyclodextrin, n is preferably a value ranging from 3 to 8 and in particular a value equal to 4.2 or 6.3, and the total number m of groups $R_1$ ranges from 2.5 to 16.

When CD represents the basic skeleton of γ-cyclodextrin, n is preferably a value ranging from 4 to 8, and the total number m of groups $R_1$ ranges from 2.5 to 18.

The value of m may be determined by the saponification number or by the NMR spectrum.

CD is preferably β-cyclodextrin.

n is preferably a statistical value ranging from 4 to 7.

The compounds according to the invention are virtually insoluble in water, the solubility decreasing as a function of the number of groups $OR_2$. They are slightly soluble in oils such as diisopropyl adipate, but more soluble in alcohols such as ethanol or isopropanol. The higher the number of groups $OR_2$ in the said compounds, the more the solubility of the compounds in alcohols decreases.

The subject of the present invention is also the process for the preparation of the compounds of formula (I). This process consists in reacting, in a solvent, (i) a substituted cyclodextrin of formula $CD(OR_2)_n(OH)_{1'}$, $OR_2$ representing a group attached to the basic skeleton of the cyclodextrin, in which $R_2$ denotes a linear or branched $C_1$–$C_4$ alkyl radical or a $C_2$–$C_4$ hydroxyalkyl radical, it being possible for the hydrogen of the hydroxyl group of the hydroxyalkyl radical to be substituted with another hydroxyalkyl group, n being a statistical value having the same meaning as above, 1' is a non-zero statistical value such that 1'+n is equal to 18, 21 or 24 depending on whether CD represents the basic skeleton of α-, β- or γ-cyclodextrin, with (ii) p moles of an acid chloride of formula Cl—$R_1$, $R_1$ denoting a radical of formula (II), (III), (IV), (V) or (VI) as defined above, p having the same meaning as above.

The reaction may be carried out in an organic solvent, especially an anhydrous one, such as pyridine or dimethylformamide.

The reaction may be carried out at a temperature between 0° C. and 80° C. and preferably between 10° C. and 30° C.

The reaction may be carried out in the presence of an acylation catalyst. This may in particular be para-N,N-dimethylaminopyridine.

The subject of the present invention is also a composition comprising at least one compound of formula (I) as defined above.

The composition preferably comprises a cosmetically acceptable medium and constitutes, in particular, a composition intended to protect the skin and/or the hair against UV and/or solar radiation.

In the compositions according to the invention, the derivatives of formula (I) may be present at a concentration which may range from 0.5% to 10% and preferably from 0.5% to 5% by weight relative to the total weight of the composition.

These compositions may contain the ingredients usually used in cosmetics. Thus, they may contain at least one constituent chosen from fatty substances, thickeners, fatty acid esters, fatty acid esters of glycerol, silicones (volatile or non-volatile, functionalized or non-functionalized), fatty alcohols, surfactants, fragrances, preserving agents, sunscreens, proteins, vitamins, polymers, organic or inorganic oils, pigments, fillers and any other additive conventionally used in the cosmetics field.

The compositions of the invention may be in any form of solution or dispersion of the derivatives as defined above, which may optionally be vesicles.

All of these compositions are prepared according to the usual methods known to those skilled in the art.

The subject of the invention is also the use of the compounds of formula (I) as defined above in, or for the manufacture of, a cosmetic composition. The subject of the invention is also the use of the compounds of formula (I) as an agent for screening out solar radiation and/or as an antioxidant.

Several examples of the preparation of compounds according to the invention will now be given by way of illustration and with no limiting nature, along with examples of cosmetic compositions containing them.

In the preparation examples, E 1% corresponds to the optical density of a solution of 1 g of compound in 100 g of solvent.

EXAMPLE 1

Preparation of a compound of formula (I) in which $R_1$ is a radical of formula (II) for which q=0, $R_4$=H, $R_2$ is a hydroxypropyl radical, n=4.2, m=3

To a solution of 1.72 g (1.25 mmol) of hydroxypropyl β-cyclodextrin (n=4.2), sold under the name Rhodocap HP by the company Rhône-Poulenc, in 20 ml of anhydrous pyridine, are added portionwise at 20° C. over 20 minutes, under a nitrogen atmosphere, 1.74 g (5.75 mmol) of 4'-benzylidenecamphorbenzoyl chloride. After stirring for 40 hours at room temperature, the reaction mixture is evaporated under reduced pressure. The residue is then taken up in ethyl ether, filtered, washed with water and dried. After purification on a column of silica (95/5 dichloromethane/methanol eluent), 2.2 g of a pale yellow powder with a melting point of 240° C. are obtained.

Infrared: ester band at 1715 $cm^{-1}$

UV (absolute ethanol): $\lambda_{max}$=300 nm; E 1%=435

EXAMPLE 2

Preparation of a compound of formula (I) in which $R_1$ is a radical of formula (III) for which $R_5$ =methyl, $R_2$ is a hydroxypropyl radical, n=6.3, m=5.7

The compound is prepared according to the same procedure as that of Example 1, using:

3 g (2 mmol) of hydroxypropyl β-cyclodextrin (n=6.3) sold by the company Aldrich 2.55 g (13.9 mmol) of para-N,N-dimethylaminobenzoyl chloride The mixture is left stirring for 24 hours. After removal of the solvent, the gum obtained is taken up in diisopropyl ether, filtered and washed with water and the solid obtained is dried. This solid is washed with hot ethanol. After crystallization, 1.6 g of a pale yellow powder with a melting point of 210° C. are obtained.

Infrared: ester band at 1715 $cm^{-1}$

UV (absolute ethanol): $\lambda_{max}$=311 nm; E 1%=635

EXAMPLE 3

Preparation of a compound of formula (I) in which $R_1$ is a radical of formula (IV) for which $R_6$=$R_7$=H, $R_2$ is a hydroxypropyl radical, n=4.2, m=4.5

The compound is prepared according to the same procedure as that of Example 1, using:

1.25 g (0.9 mmol) of hydroxypropyl β-cyclodextrin (n=4.2)

0.825 g (4.2 mmol) of para-methoxycinnamyl chloride

After purification of the residue on a column of silica (90/10 dichloromethane/methanol eluent), 1.1 g of a pale yellow powder with a melting point of 67° C. are obtained.

Infrared: ester band at 1715 $cm^{-1}$

UV (absolute ethanol): $\lambda_{max}$=307 nm; E 1%=450

EXAMPLE 4

Preparation of a compound of formula (I) in which $R_1$ is a radical of formula (IV) for which $R_6$=$R_7$=H, $R_2$ is a methyl radical, n=14.6, m=2.9

The compound is prepared according to the same procedure as that of Example 1, using:

2 g (15 mmol) of methyl β-cyclodextrin (n=14.6) sold under the name PMCD by the company Orsan 2.06 g (10.5 mmol) of para-methoxycinnamyl chloride After stirring for 100 hours, 20 ml of water and 20 ml of dichloromethane are added to the reaction medium. The organic phase is recovered and evaporated. The gum obtained is taken up in isopropyl ether, filtered and washed with water. After purification of the residue on a column of silica (98/2 dichloromethane/methanol eluent), 1.5 g of a pale yellow powder with a melting point of 185–187° C. are obtained.

Infrared: ester band at 1715 cm$^{-1}$

UV (absolute ethanol): $\lambda_{max}$=309 nm; E 1%=350

EXAMPLE 5

Preparation of a compound of formula (I) in which $R_1$ is a radical of formula (VI) for which $R_8$=tBu, s=0, $R_2$ is a hydroxypropyl radical, n=4.2, m=3.8

The compound is prepared according to the same procedure as that of Example 1, using:

27.6 g (20 mmol) of hydroxypropyl β-cyclodextrin (n=4.2)

24.8 g (92.4 mmol) of 3,5-di-tert-butyl-4-hydroxybenzoyl chloride

After purification of the residue on a column of silica (dichloromethane/methanol eluent: 98/2 and then a gradient to 85/15), 27.2 g of an off-white powder with a melting point of 255° C. are obtained.

Infrared: ester band at 1710 cm$^{-1}$

EXAMPLE 6

Preparation of a compound of formula (I) in which $R_1$ is a radical of formula (VI) for which $R_8$=tBu, s=0, $R_2$ is a hydroxypropyl radical, n=4.2, m=15

The compound is prepared according to the same procedure as that of Example 1, using:

2.78 g (2 mmol) of hydroxypropyl β-cyclodextrin (n=4.2)

12.5 g (46.5 mmol) of 3,5-di-tert-butyl-4-hydroxybenzoyl chloride

After stirring for 40 hours, the reaction medium is poured into 150 ml of ice-cold water and filtered, and the solid obtained is washed with water. After purification of the residue on a column of silica (dichloromethane/methanol eluent: 98/2 and then a gradient to 85/15), 4.3 g of an off-white powder with a melting point of 215° C. are obtained.

Infrared: ester band at 1710 cm$^{-1}$

EXAMPLE 7

Preparation of a compound of formula (I) in which $R_1$ is a radical of formula (VI) for which $R_8$=tBu, s=2, $R_2$ is a hydroxypropyl radical, n=4.2, m=3

The compound is prepared according to the same procedure as that of Example 1, using:

27.6 g (0.02 mol) of hydroxypropyl β-cyclodextrin (n=4.2)

27.4 g (0.092 mol) of 3,5-di-tert-butyl-4-hydroxyphenylpropionyl chloride

After purification of the residue on a column of silica (dichloromethane/methanol eluent: 98/2 and then a gradient to 85/15), 25.6 g of an off-white powder with a melting point of 170° C. are obtained.

Infrared: ester band at 1710 cm$^{-1}$

EXAMPLE 8

Preparation of a compound of formula (I) in which $R_1$ is a radical of formula (VI) for which $R_8$=tBu, s=0, $R_2$ is a methyl radical, n=14.6, m=3.6

The compound is prepared according to the same procedure as that of Example 1, using:

0.71 g (0.525 mmol) of methyl β-cyclodextrin (n=14.6)

1 g (3.72 mmol) of 3,5-di-tert-butyl-4-hydroxybenzoyl chloride

After removal of the solvent, the residue is washed with water and extracted with dichloromethane. After evaporation, the residue is purified on a column of silica (dichloromethane eluent) and 0.8 g of an off-white powder with a melting point of 190° C. is obtained.

Infrared: ester band at 1710 cm$^{-1}$

EXAMPLE 9

Preparation of a compound of formula (I) in which $R_1$ is a mixture of a radical of formula (VI) for which $R_8$=tBu, s=2 and a radical of formula (IV) in which $R_6$=$R_7$=H, $R_2$ is a hydroxypropyl radical, n=4.2, m=6.4 m antioxidant=2.6 m screening agent=3.8

To a solution of 2.16 g (1 mmol) of the compound of Example 7 in 15 ml of anhydrous pyridine is added, at 20° C. over 5 minutes, 0.9 g (4.6 mmol) of p-methoxycinnamyl chloride. After stirring for 40 hours under a nitrogen atmosphere, the solvent is removed under reduced pressure. The residue is taken up in isopropyl ether and then in water and is filtered. After purification of the residue on a column of silica (dichloromethane/methanol eluent: 98/2 and then a gradient to 85/15), 1.7 g of an off-white powder with a melting point of 160° C. are obtained.

Infrared: ester band at 1710 cm$^{-1}$

UV (absolute ethanol): $\lambda_{max}$=310 nm; E 1%=340

EXAMPLE 10

An antisun composition of the following formulation was prepared:

| | |
|---|---|
| - mixture of cetylstearyl alcohol and of cetylstearyl alcohol oxyethylenated with 33 mol of ethylene oxide (80/20), sold under the name "Dehsconet 390" by the company Tensia | 7 g |
| - glyceryl stearate | 2 g |
| - cetyl alcohol | 1.5 g |
| - dimethicone sold under the name "Silbione" oil 70047 V 300" by the company Rhône-Poulenc | 1.5 g |
| - liquid petroleum jelly | 15 g |
| - propylene glycol | 20 g |
| - compound of Example 3 | 5 g |
| - butyl p-hydroxybenzoate | 0.2 g |
| - imidazolidinylurea | 0.2 g |
| - demineralized water qs | 100 g |

We claim:

1. Cyclodextrin derivatives, having formula (I) below:

$$CD(OH)_l(OR_1)_m(OR_2)_n \qquad (I)$$

in which:

CD represents the basic skeleton of α-, β- or γ-cyclodextrin without the hydroxyl groups, $OR_1$ represents a group, attached to the basic skeleton of the cyclodextrin, in which $R_1$ represents a radical of formula (II), (III), (IV), (V) or (VI) below:

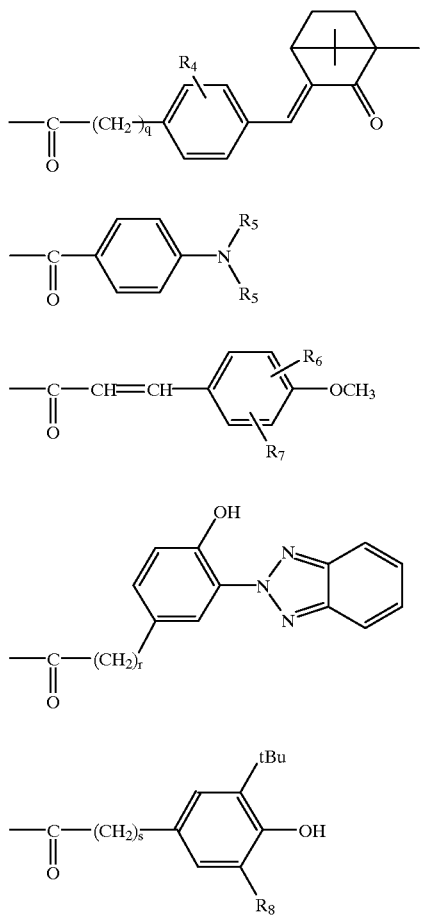

or a mixture thereof, in which formulae $R_4$, $R_6$ and $R_7$ represent a hydrogen atom or a $C_1$–$C_6$alkyl radical or a $C_1$–$C_{12}$alkoxy radical, $R_5$ represents a $C_1$–$C_{12}$alkyl radical, q and r represent an integer equal to 0 or 1, $R_8$ represents H or a $C_1$–$C_8$alkyl radical or a $C_1$–$C_4$alkoxy radical, s is an integer ranging from 0 to 4, $OR_2$ represents a group, attached to the basic skeleton of the cyclodextrin, in which $R_2$ represents a linear or branched $C_1$–$C_4$alkyl radical or a $C_2$–$C_4$hydroxyalkyl radical, wherein the hydrogen of the hydroxyl group of the said hydroxyalkyl radical is optionally substituted with another hydroxyalkyl group or with a radical $R_1$ or a mixture thereof, l, m and n are statistical values such that m represents the number of groups $OR_1$ attached directly to the basic skeleton of the cyclodextrin and is a statistical value other than 0, n represents the number of groups $OR_2$ attached directly to the basic skeleton of the cyclodextrin and is a statistical value other than 0, l is a statistical value such that (l+m+n) is equal to 18, 21, 24 depending on whether CD is the basic skeleton of α-, β- or γ-cyclodextrin respectively.

2. Cyclodextrin derivatives according to claim 1, wherein $R_2$ denotes a methyl or hydroxypropyl radical, wherein the hydrogen of the hydroxyl group of the hydroxypropyl radical is optionally substituted with another hydroxypropyl group or with a radical $R_1$.

3. Cyclodextrin derivatives according to claim 1, wherein n ranges from 3 to 5 and that the total number m of groups $R_1$ ranges from 2.5 to 14 when CD represents the basic skeleton of α-cyclodextrin; n ranges from 3 to 8 and m ranges from 2.5 to 16 when CD represents the basic skeleton of β-cyclodextrin; n ranges from 4 to 8 and m ranges from 2.5 to 18 when CD represents the basic skeleton of γ-cyclodextrin.

4. Cyclodextrin derivatives according to claim 1, wherein CD is β-cyclodextrin.

5. Process for the preparation of the cyclodextrin derivatives of formula (I), wherein
   (i) a substituted cyclodextrin of formula $CD(OR_2)_n(OH)_{l'}$ is reacted, in solution in an organic solvent, with
   (ii) m moles of an acid chloride of formula Cl—$R_1$, it being understood that:
      n and m are non-zero statistical values,
      n ranges from 3 to 5 and m ranges from 2.5 to 14 when CD represents the basic skeleton of α-cyclodextrin,
      n ranges from 3 to 8 and m ranges from 2.5 to 16 when CD represents the basic skeleton of β-cyclodextrin,
      n ranges from 4 to 8 and m ranges from 2.5 to 18 when CD represents the basic skeleton of γ-cyclodextrin,
      l' is a non-zero statistical value such that l'+n is equal to 18, 21 or 24 depending on whether CD represents the basic skeleton of α-, β- or γ-cyclodextrin,
      $OR_2$ and $R_1$ have the meaning given in claim 1.

6. Composition comprising at least one compound of formula (I) as defined in claim 1 and a cosmetically or pharmaceutically acceptable carrier.

7. Composition according to claim 6, comprising a cosmetically acceptable carrier.

8. Composition according to claim 6, wherein the compounds of formula (I) are present at a concentration ranging from 0.5% to 10% by weight relative to the total weight of the composition.

9. Composition according to claim 6, wherein said composition is capable of protecting at least one of the skin or the hair against UV radiation.

10. A method of preparing a cosmetic composition comprising combining a cosmetically effective amount of a cyclodextrin derivative of claim 1 with a cosmetically acceptable carrier.

11. A method of using a cosmetic composition, comprising topically applying to at least one of the skin or hair of a subject, a cosmetically effective amount of a cosmetic composition comprising a cyclodextrin derivative of claim 1.

12. A method for protecting at least one of the skin or hair against UV or solar radiation, said method comprising applying a composition comprising a cyclodextrin derivative of claim 1 to at least one of the skin or hair of a subject in need of such protection.

13. A method of preventing oxidation, said method comprising applying an anti-oxidative effective amount of a composition comprising a cyclodextrin derivative of claim 1 to a substrate susceptible to oxidation.

* * * * *